United States Patent [19]

Michelucci et al.

[11] Patent Number: 4,781,925

[45] Date of Patent: Nov. 1, 1988

[54] CALCIUM SUPPLEMENT COMPRESSED TABLETS

[75] Inventors: John J. Michelucci; Deborah M. Sherman, both of Plattsburgh, N.Y.; Ronald N. Warner, Grand Isle, Vt.

[73] Assignee: American Home Products Corporation, New York, N.Y.

[21] Appl. No.: 836,886

[22] Filed: Mar. 6, 1986

[51] Int. Cl.$^4$ .................. A61K 9/22; A61K 33/42
[52] U.S. Cl. ..................... 424/465; 424/128
[58] Field of Search ............. 424/468, 456, 128, 465

[56] References Cited

U.S. PATENT DOCUMENTS 4,444,769 4/1984 Blume et al. ................. 424/468
4,681,765 7/1987 Guley .......................... 424/456

FOREIGN PATENT DOCUMENTS 54333 6/1982 European Pat. Off. .
WO81/02521 9/1981 PCT Int'l Appl. .

OTHER PUBLICATIONS

Chem. Abst. 96:205,322k (1982)-Gorman et al.
Martindale-The Extra Pharmacopoeia-28th ed.-1982, The Pharm-Press-London-pp. 623-624.
Remington's-Pharmaceutical Science-15th ed.-1975 p. 770.
E. A. Gorman et al., Drug Development and Industrial Pharmacy, 8(3), 397-410 (1982).
M. N. Femi-Oyewo et al., J. Pharm. Tech. and Prod. Mfg., 3, 73-75 (1982).

Primary Examiner—Douglas W. Robinson

[57] ABSTRACT

A calcium supplement compressed tablet containing at least about 80% by weight of tricalcium phosphate having incorporated therein as a disintegrant croscarmellose sodium and about 50% to 100% by weight based on the croscarmellose sodium of sodium lauryl sulfate.

3 Claims, No Drawings

CALCIUM SUPPLEMENT COMPRESSED TABLETS

BACKGROUND OF THE INVENTION

This invention relates to calcium supplement compressed tablet compositions having improved disintegration characteristics. More particularly, this invention relates to calcium supplement compressed tablet compositions containing as a disintegrant croscarmellose sodium and about 50% to 100% by weight based on the croscarmellose sodium of sodium lauryl sulfate.

Calcium supplement compressed tablets are well known to the art and commonly contain tricalcium phosphate or a mixture thereof with dicalcium phosphate, a binder such as microcrystalline cellulose, a disintegrant such as sodium starch glycolate or croscarmellose sodium, and a lubricant such as magnesium stearate. See for example, Kanig et al, International Application Published Under The Patent Cooperation Treaty (PCT), International Publication No. WO 81/02521, published Sept. 17, 1981, and Gerard European Patent Application Publication No. 54333, published June 23, 1982. These publications, hereby incorporated by reference in their entirety, describe roller compacting at a pressure of from 300 to 1000 atmospheres of fine particles of calcium phosphate alone or admixed with microcrystalline cellulose, comminuting the resulting ribbons or sheets of compacted material and using the resulting comminuted granules as excipients for pharmaceutical tablets.

SUMMARY OF THE INVENTION

This invention relates to calcium supplement compressed tablet compositions containing microcrystalline cellulose and at least 80% by weight of calcium phosphate with improved disintegration characteristics by having incorporated therein a disintegrant mixture of croscarmellose sodium and 50 to 100% by weight based on the croscarmellose sodium of sodium lauryl sulfate.

Accordingly, the calcium supplement compressed tablets of this invention consist essentially of at least about 80% by weight calcium phosphate, preferably as tricalcium phosphate, about 6% to 12% by weight of microcrystalline cellulose, about 0.5 to about 1% by weight croscarmellose sodium up to about 0.5% by weight of a lubricant such as magnesium stearate and about 0.5% to 1% by weight sodium lauryl sulfate, the amount of sodium lauryl sulfate being about 50% to about 100% by weight based upon the weight of croscarmellose sodium.

The calcium phosphate can be of commercial compacted grade. A suitable compacted grade of tricalcium phosphate is marketed by Stauffer Chemical Company of Westport, Conn. U.S.A. as TRI-TAB® containing about 37.5% elemental calcium by weight.

Microcrystalline cellulose is commercially available and a suitable grade is for example, the material sold as Avicel-PH-101 (available from FMC Corporation, American Viscose Division, Avicel Sales, Marcus Hook, Pa., U.S.A.).

Croscarmellose sodium is the sodium salt of a polycarboxymethyl ether of cellulose. It is sold under the trade name AcDiSol and is available from FMC Corporation, 200 Market St., Philadelphia, Pa. 19103, U.S.A.

Sodium lauryl sulfate and the magnesium stearate lubricant commercially available in USP and NF grades. Other lubricants such as stearic acid and aluminum stearate are also commercially available in NF grade.

By the term calcium supplement tablet is meant a calcium tablet containing at least about 80% calcium phosphate which is taken supplementary to the normal diet as an aid in alleviating certain bone deficiencies.

DETAILED DESCRIPTION OF THE INVENTION

This invention is based upon the observation that conventional calcium supplement compressed tablets containing compacted tricalcium phosphate, microcrystalline cellulose and about 0.5% croscarmellose sodium demonstrated an unexpected aging phenomenon in that the tablets were found to have unacceptable disintegration times after two weeks storage at various stress storage conditions although the fresh tablets exhibited satisfactory disintegration times.

This unexpected aging phenomenon could be overcome by incorporating croscarmellose sodium levels in excess of 1% of the tablet weight, but initial tablet disintegration was so fast that it made swallowing the tablet difficult.

The invention, however, resides in the empirical finding that the addition of about 50% to 100% sodium lauryl sulfate based upon the weight of croscarmellose sodium to such a calcium supplement compressed tablet minimized the tablet disintegration aging phenomenon while at the same time providing a tablet with acceptable disintegration characteristics for easy swallowing.

The invention will be further illustrated by the examples in which the tablets were prepared using the procedure outlined below.

Procedure

1. Blend tricalcium phosphate, microcrystalline cellulose and croscarmellose sodium in suitable mixer (V-Blender) until uniform.
2. Add magnesium stearate to blend in Step #1 and blend until distributed.
3. Compress blend using capsular shaped tooling to a hardness of 17-21 SCU (strong cobb units).

EXAMPLE 1

A conventional 600 mg calcium supplement compressed tablet was prepared following the above procedure and having the composition given below:

| Ingredients | Amount/ Tablets | -Percent of Tablet Weight |
|---|---|---|
| Tricalcium Phosphate (Tri-Tab) @ 38% elemental calcium | 1579.0 mg | (91.5%) |
| Microcrystalline Cellulose, N.F. | 129.43 mg | (7.5%) |
| Croscarmellose Sodium, N.F. | 8.63 mg | (0.5%) |
| Magnesium Strarate, N.F. | 8.63 mg | (0.5%) |
| Theoretical Tablet Weight | 1726 mg | |

The above tablets were packaged in standard high density polyethylene bottles, 75 to 100 tablets to the bottle, and stored under various stress conditions set forth in Table 1 below. After the times indicated in the table, the tablets were placed in the USP Disintegration Apparatus and subjected to disintegration conditions for plain tablets in accordance with the USP Method for Compressed Tablets found in the 1985 U.S. Pharmacopoeia 21 and National Formulary 16 at Section 701 (n=6). The results which appear below in Table 1, show that the tablets have unacceptable disintegration times of greater than 30 minutes.

TABLE 1

| Storage Condition | Ave. Disintegration Time |
|---|---|
| Initial | All ≦ 90 seconds |
| *2 wks @ 62° C.-Packaged | All > 30 minutes |
| 2 wks @ 80% R.H./27° C.-Exposed | All > 30 minutes |
| 2 wks @ 75% R.H./40° C.-Exposed | All > 30 minutes |
| *2 wks @ 40° C.-Packaged | All > 30 minutes |

*Packaged with metal cap.

EXAMPLE 2

In accordance with the invention, three batches of 600 mg calcium supplement compressed tablets were prepared using the procedure and having the composition given below:

Procedure
1. Blend compacted tricalcium phosphate, microcrystalline cellulose, croscarmellose sodium and sodium lauryl sulfate in suitable mixer (V-Blender) until uniform.
2. Add magnesium stearate to the blend in Step #1 and blend until distributed.
3. Compress blend on capsular shaped tooling to a hardness of 17-21 SCU (strong cobb units).

The figure in each of the first columns represents the amount in milligrams of the ingredient per tablet and the figure in each of the second columns represents the percent of tablet weight of each ingredient.

| Ingredients | Batch #1 | Batch #2 | Batch #3 |
|---|---|---|---|
| Tricalcium Phosphate (Tri-Tab) @ 37.5% Calcium | 1604.0 (91.25%) | 1604.0 (91.25%) | 1604.0 (91.0%) |
| Microcrystalline Cellculose, N.F. | 131.8 (7.5%) | 131.8 (7.5%) | 132.2 (7.5%) |
| Croscarmellose Sodium, N.F. | 4.4 (0.25%) | 8.8 (0.5%) | 8.8 (0.5%) |
| Sodium Lauryl Sulfate, N.F. | 8.8 (0.5%) | 4.4. (0.25%) | 8.8 (0.5%) |
| Magnesium Stearate, N.F. | 8.8 (0.5%) | 8.8 (0.5%) | 8.8 (0.5%) |
| Theoretical Tablet Weight | 1758 mg | 1758 mg | 1763 mg |

Again, the tablets were packaged in standard high density polyethylene bottles with metal caps, 75 to 100 to the bottle, and stored under various stress conditions set forth in Table 2 below. After the times indicated in the table, the tablets were placed in USP Disintegration Apparatus and subjected to disintegration conditions as above in Example 1.

The results appear below in Table 2.

TABLE 2

| | Ave Disintegration Time formula # | | |
|---|---|---|---|
| Storage Condition | #1 | #2 | #3 |
| Initial | 3 min, 30 sec | 1 min, 15 sec | 1 min |
| 1 wk @ 40° C. | 10 min | 15 min | 1 min, 30 sec |
| 1 wk @ 51° C. | 15 min | >30 min | 2 min |
| 1 wk @ 62° C. | — | — | — |
| 2 wks @ 40° C. | 15 min | — | 1 min, 30 sec |
| 2 wks @ 51° C. | 30 min | — | 2 min |
| 2 wks @ 62° C. | — | — | 25 min |

The above results surprisingly show that a combination of 0.5% sodium lauryl sulfate with 0.5% croscarmellose sodium significantly minimizes the tablet disintegration aging phenomenon observed in the same formula without the surfactant added.

In addition to the calcium phosphate, the microcrystalline cellulose, the croscarmellose sodium and sodium lauryl sulfate disintegrant and the lubricant, relatively small amounts of conventional filler materials from about 1% to about 10% by weight of the tablet can be employed. For example, the addition of about 5% by weight of a high molecular weight solid polyethylene glycol, preferably a type 8000 powdered, can be advantageous to help prevent the calcium phosphate from sticking to indented portions of the punch face during compression.

Also, the tablets can be coated with a thin clear film coating, organic solvent or aqueous based, to provide for easy swallowing and a more elegant product.

We claim:

1. A calcium supplement compressed tablet having improved disintegration characteristics comprising at least about 80% by weight of compacted calcium phosphate, and as a disintegrant about 0.5 to less than 1% croscarmellose sodium and about 0.5 to about 1% by weight of sodium lauryl sulfate, the amount of sodium lauryl sulfate being about 50% to about 100% by weight based upon the weight of croscarmellose sodium.

2. A calcium supplement compressed tablet having improved disintegration characteristics consisting essentially of at least about 80% by weight of compacted tricalcium phosphate, about 6% to about 12% by weight of microcrystalline cellulose, about 0.5 to about 1% by weight croscarmellose sodium and about 0.5% to 1% by weight of sodium lauryl sulfate, the amount of sodium lauryl sulfate being about 50% to about 100% by weight based upon the weight of croscarmellose sodium, and up to about 0.5% by weight of a lubricant.

3. A calcium supplement compressed tablet having improved disintegration characteristics consisting of 91.0% by weight compacted tricalcium phosphate, 7.5% by weight microcrystalline cellulose, 0.5% by weight croscarmellose sodium, 0.5% by weight sodium lauryl sulfate and 0.5% by weight magnesium stearate.

* * * * *